(12) United States Patent
Guzman Sanchez et al.

(10) Patent No.: US 9,463,025 B2
(45) Date of Patent: Oct. 11, 2016

(54) HERMETIC OCCLUSION SURGICAL CLAMP FOR THE CERVIX IN CASES OF PLACENTA PREVIA

(71) Applicants: Arnoldo Guzman Sanchez, Jalisco (MX); Eduardo Rodriguez De Anda, Jalisco (MX)

(72) Inventors: Arnoldo Guzman Sanchez, Jalisco (MX); Eduardo Rodriguez De Anda, Jalisco (MX)

( * ) Notice: Subject to any disclaimer, the term of this patent is extended or adjusted under 35 U.S.C. 154(b) by 286 days.

(21) Appl. No.: 14/365,683

(22) PCT Filed: Nov. 27, 2012

(86) PCT No.: PCT/MX2012/000121
§ 371 (c)(1),
(2) Date: Jun. 16, 2014

(87) PCT Pub. No.: WO2013/089545
PCT Pub. Date: Jun. 20, 2013

(65) Prior Publication Data
US 2014/0336683 A1    Nov. 13, 2014

(30) Foreign Application Priority Data

Dec. 16, 2011  (MX) .................... MX/a/2011/013931

(51) Int. Cl.
*A61B 17/42* (2006.01)
*A61B 17/122* (2006.01)
*A61B 17/12* (2006.01)

(52) U.S. Cl.
CPC ......... *A61B 17/122* (2013.01); *A61B 17/1227* (2013.01); *A61B 2017/12004* (2013.01); *A61B 2017/4225* (2013.01)

(58) Field of Classification Search
CPC ............ A61B 17/122; A61B 17/1227; A61B 2017/12004; A61B 2017/4225
See application file for complete search history.

(56) References Cited

U.S. PATENT DOCUMENTS

2002/0107533 A1*  8/2002  Solingen .............. A61B 17/122
                                                                   606/151

FOREIGN PATENT DOCUMENTS

| ES | 2261436 | 4/2003 |
|---|---|---|
| ES | 2297579 | 3/2006 |
| FR | 2805146 | 8/2001 |
| GB | 2465615 | 6/2010 |
| WO | WO8806867 | 9/1988 |

* cited by examiner

*Primary Examiner* — Gregory Anderson
(74) *Attorney, Agent, or Firm* — Defillo & Associates, Inc.; Evelyn A. Defillo

(57) ABSTRACT

The present invention relates to a hermetic occlusion surgical clamp for the female cervix to be used in case of placenta previa, including compression jaws with a spring (5.1) and semi-conical sections (5.2) and at the end of each jaw a machined semi-cylinder (5.3), and a pull-down cylinder with a machining that generated two arms (6.2) with a hole that is joined by a pin (5.4) that connects the jaws to the pull-down cylinder. The pull-down cylinder also includes a thread (6.4), which allows you to screw on a screw (6.5) to open or close the jaws. Finally, the surgical clamp also includes a shell which is a hollow cylinder along its longitudinal axis, which covers semi-conical sections (5.2) of the jaws to leave a thread length (6.4) free that allows placement of the screw (6.5).

5 Claims, 3 Drawing Sheets

HERMETIC OCCLUSION SURGICAL CLAMP FOR THE CERVIX IN CASES OF PLACENTA PREVIA

CROSS REFERENCE TO RELATED APPLICATION

This application is a national stage entry of PCT/MX2012/000121 filed Nov. 27, 2012, under the International Convention claiming priority over Mexican Application No. MX/a/2011/013931 filed Dec. 16, 2011.

FIELD OF THE INVENTION

The present invention relates to an occlusion clamp surgically used for sealing the cervix. It is a mechanical device that seals the passage of the cervix, and prevents blood leakage through the passage during the operation of a patient with placenta previa bleeding.

BACKGROUND OF THE INVENTION

There is no specific tool to seal the cervix passage, during the operation performed for placenta previa.

Although there are some surgical clamps, called Pozzi as shown in FIG. 1, or the Museux (see FIG. 2) or the Allis (see FIG. 3) and also the Lahey (see FIG. 4), these clamps do not fulfill the purpose of producing the tight occlusion which we are referring to, and also the design of these damps causes damage to both the vaginal tissue and the cervix. It is also especially difficult with these clamps to fully embrace the cervix with enough pressure to occlude it.

On the contrary, the present invention achieves a hermetic occlusion of the passage of the cervix, and its design produces no injury to either the vagina not the cervix. In addition, it has the suitable dimensions for the space it occupies in the vaginal canal and its surroundings.

Since we started using the occlusive clamp, we did not have any bleeding through the passage of the cervix.

Problem to Solve

Reduce maternal death by bleeding. The World Health Organization blames maternal bleeding to be the leading cause of maternal death in Latin America, which is a tragedy.

The World Health Organization's fifth objective literally states, That "We must reduce the maternal death," a goal that must be attended.

How to Solve the Problem

The problem of bleeding that we are referring to, we have resolved it by utilizing the hermetic occlusion clamp of the female cervix, which is proposed by the present invention, in cases of placenta previa.

By achieving a hermetic occlusion of the cervix passage, through using the clamp of our present invention, you will manage to stop the blood flow that drains through the cervix passage; this blood originates from a small portion of the placenta that is detached from the internal side of the matrix.

When the hermetic occlusion of the cervix passage manages to stop the blood flow, what happens is that the blood accumulates between the occluded section and the site that generates the bleeding that comes from the insertion site of the placenta which has partially collapsed.

The above mechanism balances the output blood pressure from the placenta with the pressure generated due to the accumulation of blood in the space between the site of the occlusion of the clamp and the outflow of blood. This prevents more blood flow into the space mentioned before. The experience gained from 66 surgeries, in which the clamp of the present invention was applied, demonstrates the utility of the tool in function that has not led to any bleeding through the cervix passage.

DETAILED DESCRIPTION OF THE INVENTION

The present invention proposes a hermetic occlusion clamp for the female cervix in cases of placenta previa. The clamp is essentially cylindrical. It includes three mutually assembled main parts, which are:
1. Compression jaws, see FIG. 5.
2. Pull-down cylinder, see FIG. 6.
3. Shell, see FIG. 7.

1.—Compression jaws, see FIG. 5: These are the elements responsible for compressing the female cervix to occlude it. These jaws are initially separated by the action of an expander spring (5.1). The compression ends of the jaws open wide enough to catch the cervix. At the opposite ends, each jaw has a semi-conical section (5.2) and also each semi-conical segment (5.2) has a drilled semi-cylinder (5.3), which overlaps each other and are joined with a pin (5.4) to the pull-down cylinder, see FIG. 6, the pin (5.4) serves as the axis of rotation of both jaws, FIG. 5.

Furthermore, both jaws have a serrated section with pointed ends, which do not make contact when approaching end to end, but rather alternate the positions of the teeth of the upper jaw with respect to the teeth of the lower jaw. The ends of the teeth may have different shapes, Also, the expander spring (5.1) may be replaced by any other element that causes the separation of the jaws.

Also, the semi-conical segments (5.2) of the jaws may be of any other form. In the same way, the overlap of the semi-cylinder sections (5,3) of each jaw may have different forms of assembly.

Also, the pin (5.4) which connects the jaws may be replaced by any other element that performs the same functions.

2.—Pull-down cylinder, see FIG. 6: This cylinder at one end has a machining semi-elliptical space (6.1) sufficient to accommodate the semi-cylinders (5.3) of the jaws, FIG. 5. The machining of the semi-elliptical space (6.1) generates two arms (6.2) which each have a hole, in which the pin is assembled (5.4), which serves to hold the two semi-cylinders (5.3) of the jaws, FIG. 5, the pull-down cylinder, FIG. 6; which allows the rotation of the jaws about the axis of the pin (5.4). On the exterior part of the same end, it is machined a groove (6.3) which engages the pin of the shell (7.1), located on the inside of the shell, see FIG. 7. This engagement prevents the rotation of the jaws, on the longitudinal axis of the pull-down cylinder, FIG. 6, when assembled with the shell, FIG. 7: this prevents the possible injury of the cervix, when closing the jaws to hermetically occlude the cervix. The opposite end of the pull-down cylinder, FIG. 6, has a thread (6.4), which can be screwed by a screw (6.5), which when rotated allows to open or close the jaws when assembled by the jaws, the pull-down cylinder, and the shell, see FIG. 8.

In addition, the thread (6.4) of the pull-down cylinder, FIG. 6, may be standard, millimeter, or any other type of threading. Also, the bolt (7.1) of the shell and the groove (6.3) the pull-down cylinder, FIG. 6, may be configured in any other manner, including modifications of any constituent part of the cervix occlusion clamp.

In addition to the pull-down cylinder, FIG. 6 may be replaced by any other element or drive system.

3. The shell, FIG. 7: this element is a hollow cylinder all along its longitudinal axis, which covers from the semi-conical sections (5.2) of the jaws, FIG. 5, to leave a free length of the thread (6.4) that allows the placement of the screw (6.5). At one end of the shell there is a conical section (7,2), in which internal sections are coupled the semi-conical sections (5.2) of the jaws, FIG. 5. This coupling allows the separation or approximation of the jaws, FIG. 5, by rotating the screw (6.5) in either direction. In the internal section of the shell, FIG. 7, is found the bolt (7.1) of the shell, as previously described.

In addition, both shell and screw have an anti-skid finish.

In addition, each one of the constituent parts of the occlusion clamp has the possibility to be morphologically changed in such a way that it may perform the same functions of the clamp.

The integral mechanism of why jaws are closed (or separated) to achieve the hermetic occlusion of the cervix:

The closing of the jaws, FIG. 5, occurs when turning the screw (6.5), in the clockwise direction. The screw (6.5) is used as a support area for the ends (7.3) of the shell. This causes that the pull-down cylinder, FIG. 6, gradually inserts the semi-conical sections (5.2) of the jaws, FIG. 5, in the conical section (7.2) of the shell, FIG. 7, causing the closure of the jaws, FIG. 5, to the desired pressure.

On the contrary, the rotation of the screw (6.5) counter-clockwise, separates the jaws, FIG. 5, freeing the cervix of the previously mentioned pressure.

BRIEF DESCRIPTION OF THE FIGURES

Part (3): rings for clamping and controlling of the opening or closing of the arms of the clamps.
Part (4): slots for gripping and adjusting the pressure on the tip of the clamp.

Figure 1:
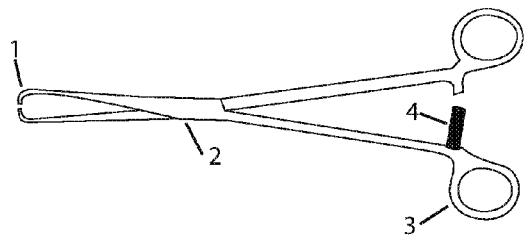
FIG. 1, Pozzi's Clamp:
Part (1): Tip of the clamp; characterized by having two puncture elements (one in each arm),
Part (2): axis of rotation, which allows the opening and closing of the arms of the clamps.
Part (3): rings for clamping and control of the opening or closing of the arms of the clamps.
Part (4): slots for and gripping and adjusting the pressure on the tip of the clamp.
Figure 2:
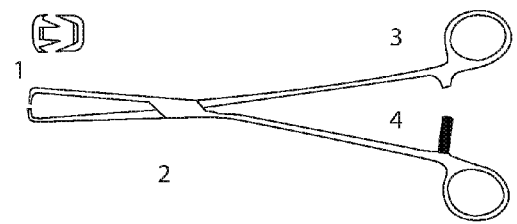
FIG. 2, Museux's clamp:
Part (1): Tip of the clamp; characterized by having two piercing elements in each one of the arms.
Part (2): axis of rotation for allowing the opening or closing of the arms of the clamp.
Part (3): rings for clamping and controlling the opening or closing of arms of the clamps.
Part (4): slot for gripping and adjusting the pressure of the ends of the clamp.
Figure 3:
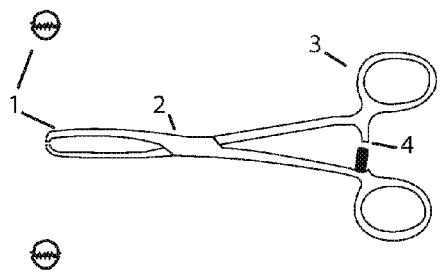
FIG. 3, Allis clamp:
Part (1): tip of the clamp, characterized by having small slots in each one of the arms.
Part (2): axis of rotation, which allows opening and closing of the arms of the clamp.
Part (3): rings for clamping and controlling the opening or closing of the arms of the clamp.
Part (4): slots for gripping and adjusting the pressure on the tip of the clamp.
Figure 4:
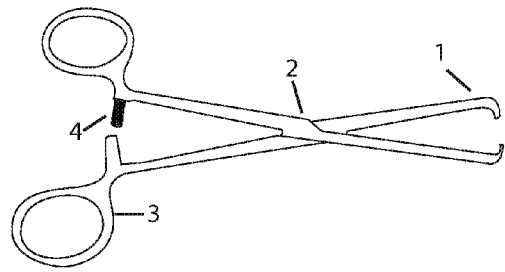
FIG. 4, Lahey's clamp:
Part (1): tip of the clamp, characterized by having three puncture elements on each one of the arms.
Part (2): axis of rotation, which allows opening and closing of the arms of the clamp.
Figure 5:
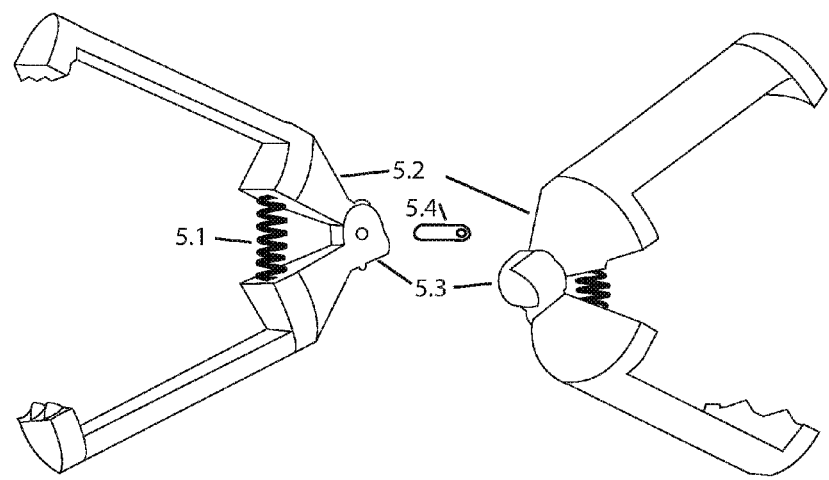
FIG. 5, compression jaws.
Figure 6:
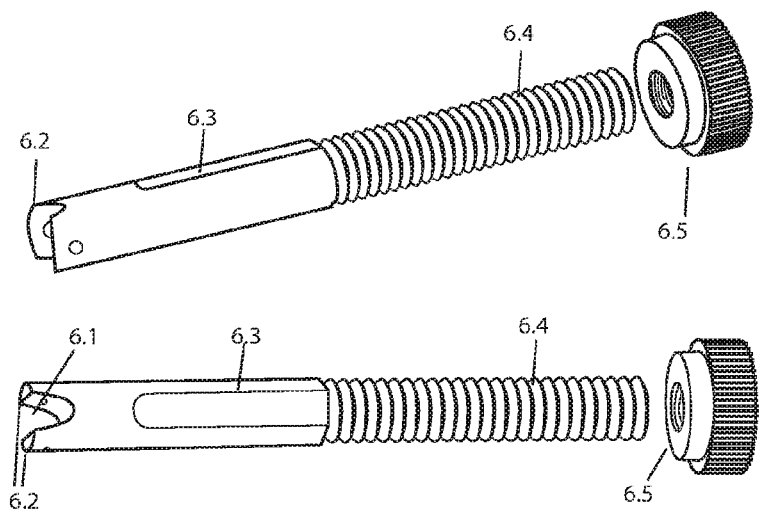
FIG. 6, pull-down cylinder.
Figure 7:
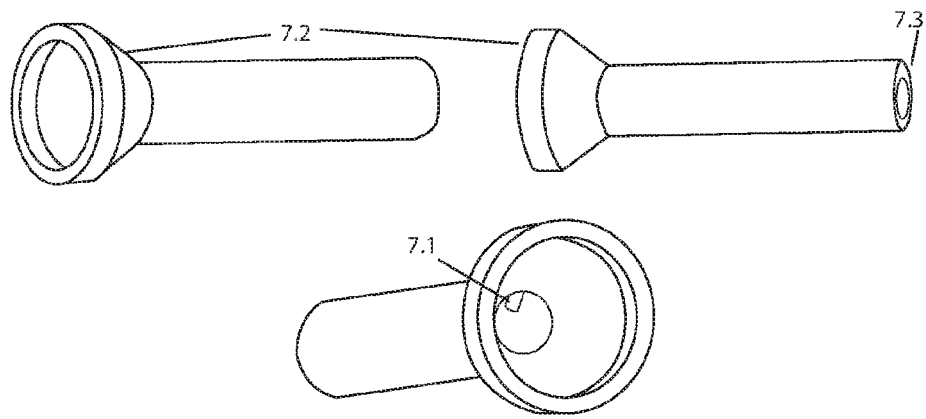
FIG. 7, shell.
Figure 8:
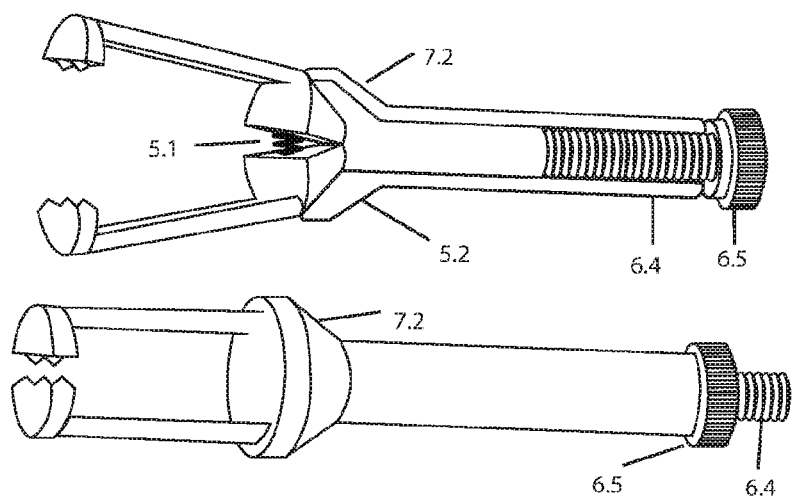
FIG. 8, the assembly of the total number of parts which constitute the hermetic occlusion surgical damp.

The following claims are based on the problem of bleeding by placenta previa, which is a serious complication that occurs during a caesarean section, to which the present invention is offering an alternative solution that had been experienced in Hospital Civil Fray Antonio Alcalde, Guadalajara Jalisco.

The Review of our previous experiences does not show that there are devices that solve this problem.

Having described the present invention, consider it to be a novelty and claim it to be my property in the following claims.

The invention claimed is:

1. A hermetic occlusion surgical clamp for a female cervix in case of placenta previa comprising:
   two compression jaws, the compression jaws are separate by an expander spring, the compression jaws includes a semi-conical section at one end of each compression jaw; a semi-cylinder drilled on each one of the semi-conical section, the semi-cylinders overlap each other and are joined by a pin, the pins serves as an axis of rotation of the jaws;
   a pull-down cylinder having a first end; a second end; a machining semi-elliptical space on a first end to accommodate the semi-cylinders of the compression jaws, each one of the machining semi-elliptical sections forms two arms, each arm includes a hole in which the pin is assembled to attach the semi-cylinders of the compression jaws to the pull-down cylinder, which allows for rotation of the compression jaws on the axis of rotation of the pin; a groove located on an exterior part of the first end; a thread located on the second end of the pull-down cylinder; a screw secured to the thread;
   a hollow shell, the hollow shell having a conical section on a first end, a second end having a cylindrical shape, and a bolt located on an internal section of the shell;
   the conical section of the hollow shell are coupled to the semi-conical sections of the compression jaws;
   when the pull-down cylinder is assembled inside the hollow shell:
   the first end of the pull-down cylinder is placed on the conical section of the hollow shell and contacting the semi-conical section of the compression jaws; and
   the thread of the pull-down cylinder is placed on the second end of the hollow shell; and
   the moving the screw in a first direction closes the compression jaws and moving the screw on a second direction opens the compression jaws.

2. The hermetic occlusion surgical clamp according to claim 1, wherein the thread of the pull-down cylinder is a standard or a millimeter thread.

3. The hermetic occlusion surgical clamp according to claim 1, wherein the compression jaws include a serrated teeth and a pointed end, wherein when the compression jaws approach each other, the teeth of one of the compression jaws are alternate positioned with respect to the teeth of the other compression jaw.

4. The hermetic occlusion surgical according to claim 1, wherein the hollow shell includes an anti-skid finish.

5. The hermetic occlusion surgical according to claim 1, wherein the screw includes an anti-skid finish.

\* \* \* \* \*